(12) United States Patent
Shah et al.

(10) Patent No.: US 11,208,247 B2
(45) Date of Patent: Dec. 28, 2021

(54) PACKAGING FOR SOLID DOSAGE FORMS OF MELATONIN WITH A HIGH CITRIC ACID CONCENTRATION

(71) Applicant: Société des Produits Nestlé S.A., Vevey (CH)

(72) Inventors: Syed M. Shah, Boca Raton, FL (US); Daniel Hassan, Boca Raton, FL (US); Fred Hassan, Boca Raton, FL (US)

(73) Assignee: Société des Produits Nestlé S.A., Vevey (CH)

(*) Notice: Subject to any disclaimer, the term of this patent is extended or adjusted under 35 U.S.C. 154(b) by 149 days.

(21) Appl. No.: 16/046,324

(22) Filed: Jul. 26, 2018

(65) Prior Publication Data
US 2019/0031417 A1    Jan. 31, 2019

Related U.S. Application Data

(60) Provisional application No. 62/539,102, filed on Jul. 31, 2017.

(51) Int. Cl.
*B65D 75/36* (2006.01)
*A61J 1/03* (2006.01)
*A61K 31/4045* (2006.01)
*A61K 9/28* (2006.01)
*B65D 75/32* (2006.01)
*A61K 9/20* (2006.01)

(52) U.S. Cl.
CPC ............ *B65D 75/366* (2013.01); *A61J 1/035* (2013.01); *A61K 9/2013* (2013.01); *A61K 9/2054* (2013.01); *A61K 9/2059* (2013.01); *A61K 9/2813* (2013.01); *A61K 31/4045* (2013.01); *B65D 75/326* (2013.01)

(58) Field of Classification Search
CPC ... A61J 1/035; A61K 31/4045; A61K 9/2813; A61K 9/2013; A61K 9/2054; A61K 9/2059; B65D 75/366; B65D 75/326
See application file for complete search history.

(56) References Cited

U.S. PATENT DOCUMENTS 5,883,161 A     3/1999  Wood et al.
6,432,448 B1 *  8/2002  Augello .............. A61K 9/286
                                                  424/479

(Continued)

FOREIGN PATENT DOCUMENTS

WO      2008014862 A1     2/2008

OTHER PUBLICATIONS

PVDC new developments, by Kirk Paisley, 2007 PLACE conference.*

*Primary Examiner* — Yan Lan
(74) *Attorney, Agent, or Firm* — Christopher M. Ramsey; GrayRobinson, P.A.

(57) ABSTRACT

Melatonin tablets with a high concentration of citric acid are packaged in a blister package that enhances storage stability. Such a packaging material includes a blister film forming a cavity holding the tablet therein. The blister film includes a polyvinyl chloride (PVC) film having a thickness of 180 μm to 270 μm coated with a polyvinylidene chloride (PVDC) coating having a coating weight of 110 g/m² to 130 g/m². An aluminum foil lid closes the cavity and encapsulates the tablet within the blister film and lid. The lid has a thickness of 20 μm to 30 μm.

14 Claims, 1 Drawing Sheet

(56) References Cited

U.S. PATENT DOCUMENTS

| | | | |
|---|---|---|---|
| 2005/0118202 A1 | 6/2005 | Yamashita et al. | |
| 2013/0122085 A1* | 5/2013 | Dalton | A61P 3/10 424/451 |
| 2016/0243038 A1* | 8/2016 | Shah | A61K 9/2054 |
| 2017/0304150 A1* | 10/2017 | Gumudavelli | B01J 20/103 |

* cited by examiner

PACKAGING FOR SOLID DOSAGE FORMS OF MELATONIN WITH A HIGH CITRIC ACID CONCENTRATION

CROSS-REFERENCE TO RELATED APPLICATION

This claims the benefit of priority from U.S. provisional Application No. 62/539,102, filed Jul. 31, 2017, which is incorporated by reference in its entirety

FIELD

This relates to the field of melatonin packaging and, more particularly, to packing of melatonin dosage forms that include a high concentration of citric acid.

BACKGROUND

In pharmaceuticals, the "primary packaging" is the packaging that immediately contacts the pharmaceutical dosage form. Examples of primary packaging include bottles, closure liners, syringes, blister films, and foils. The primary packaging provides a barrier for maintaining the product's integrity before use.

Blister packaging is commonly used for packaging solid dosage forms because it allows for a single dosage form to be removed without contaminating the other dosage forms. A blister package typically includes a blister film that forms a cavity containing the dosage form and a lidding foil that seals the cavity and is affixed to the blister film. The materials used for blister packaging are selected based on the properties of the dosage form. Different types of blister packaging can be gas and/or moisture impermeable, for example.

BRIEF SUMMARY

The storage stability of conventional melatonin pharmaceutical dosage forms containing a relatively high concentration of citric acid may be impaired because the citric acid affects the primary packaging materials, causing them to become discolored over time. Further, because citric acid is hygroscopic, it can absorb moisture through the packaging and impair the stability of the dosage form itself over time.

It would be advantageous to have primary packaging adapted for use with solid melatonin dosage forms including at least 5% w/w citric acid that has extends the shelf life of such dosage forms. Such a primary packaging includes a blister film advantageously made of a specific low moisture permeability composite material. This material may be made from one or more layers of polymer films and/or metal foils.

An example of product including the advantageous packaging material includes an oral tablet dosage form including melatonin and at least 5% w/w citric acid in a polymer matrix. The tablet is enclosed in a blister film forming a cavity holding the tablet therein. The blister film includes a polyvinyl chloride (PVC) film having a thickness of 180 µm to 270 µm coated with a polyvinylidene chloride (PVDC) coating having a coating weight of 110 g/m² to 130 g/m². An aluminum foil lid closes the cavity and encapsulates the tablet within the blister film and lid. The lid has a thickness of 20 µm to 30 µm.

Another example of such a product includes an oral tablet dosage form including melatonin and citric acid in a polymer matrix, the tablet being enclosed in a packaging material. The packaging material consists of a blister film forming a cavity holding the tablet therein, the blister film including a polyvinyl chloride (PVC) film having a thickness of 180 µm to 270 µm coated with a polyvinylidene chloride (PVDC) coating having a coating weight of 110 g/m² to 130 g/m². The packaging material further consists of an aluminum foil lid closing the cavity and encapsulating the tablet within the blister film and lid, the lid having a thickness of 20 µm to 30 µm.

Additional optional features of these examples include those now described.

The PVC film may have a thickness of 190 µm to 260 µm.

The PVDC coating may have a coating weight of about 120 g/m².

The lid may have a thickness of about 25 µm.

The PVC film may have a thickness of 190 µm to 260 µm, the PVDC coating may have a coating weight of about 120 g/m², and the lid may have a thickness of about 25 µm.

The tablet may include an opalescent outer coating containing mica particles as a light barrier.

DETAILED DESCRIPTION OF EXAMPLE EMBODIMENTS

The packaging material discussed here may be used to enhance the storage stability of an oral solid tablet dosage form that includes melatonin and citric acid. Such an oral solid dosage form includes melatonin in combination with a relatively high concentration of at least 5% w/f of the tablet of citric acid in a polymer matrix. When swallowed, the polymer matrix absorbs water and encapsulates the melatonin in a hydrogel. The acid dissolves in the hydrogel to maintain an acidic pH in the hydrogel as it travels through the subject's gastrointestinal tract. The acidic pH maintains the melatonin in a soluble form. This dosage form provides a controlled release of melatonin that is at least partially independent of pH variations in the gastrointestinal tract. Such a melatonin composition is described in U.S. Pat. No. 8,691,275, which is incorporated by reference.

Figure 1:
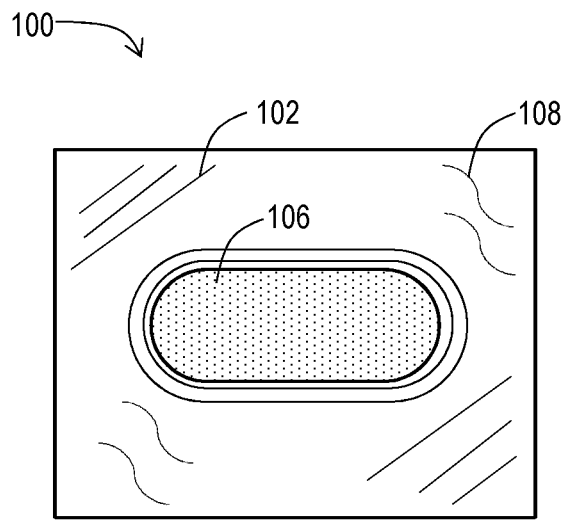
FIG. 1 is a top view of a tablet including melatonin and a high concentration of citric acid in an advantageous blister package.
Figure 2:
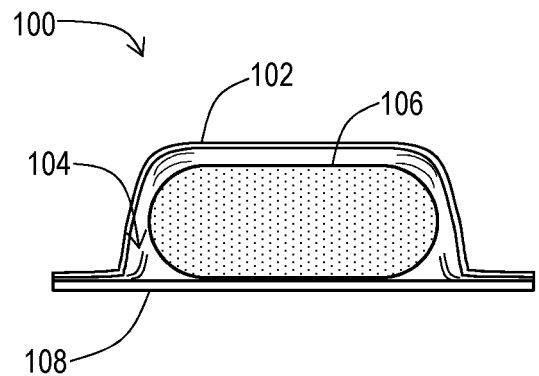
FIG. 2 is a side view thereof.

Referring to FIGS. 1 and 2, a blister package 100 including a blister film 102 that forms a cavity 104 containing the tablet 106. A lidding foil 108 seals the cavity and is affixed to the blister film 102.

The blister film 102 may be made of a composite structure including layers of polymer films and/or other materials, such as metal foils.

The blister film 102 may be transparent so that the tablet 106 is visible as shown in FIGS. 1 and 2. In FIG. 1, the lidding foil 108 is visible through the blister film 102 as indicated by the curved, dotted lines.

Some examples of polymer materials that may be used to make the polymer film(s) include, but are not limited to: polyvinyl chloride (PVC), polyvinylidene chloride (PVDC), polypropylene (PP), polychlorotrifluoroethylene (PCTFE), cyclic olefin copolymers (COC), cyclic olefin polymers (COP), polyamide, polyethyleneterephthalate glycol (PETG), and polyethylene (PE).

PVC may be used a base substrate for the blister film 102 because PVC has good thermoforming properties and conforms with many packaging regulations. But the moisture permeability of PVC alone is too high to be used as the sole blister film material. The thickness of the PVC film may be 125 μm to 500 μm, 150 μm to 300 μm, 180 μm to 270 μm, or 190 μm to 260 μm.

The blister film 102 may include a PVDC film laminated to a PVC film. The PVC/PVDC composite film has low moisture permeability and oxygen barrier properties, depending on the coating weight. The PVDC film may be added to the PVC layer by coating the PVC layer with PVDC. The amount of PVDC may be expressed in terms of coating weight in grams per square meter ($g/m^2$), Examples of coating weights of PVDC are 40 $g/m^2$ to 150 $g/m^2$, 100 $g/m^2$ to 150 $g/m^2$, 110 $g/m^2$ to 130 $g/m^2$, or about 120 $g/m^2$. The thickness of the PVDC layer may be 100 μm to 500 μm.

The blister film 102 may include a PE layer between a PVC layer and a PVDC layer. The PE layer may assist when forming deeper cavities in the blister film. The thickness of the PE layer may be 5 μm to 50 μm.

The blister film 102 may include a PCTFE film laminated to a PVC film. The thickness of the PCTFE film may be 10 μm to 250 μm.

A PE film may be formed between a PVC film and PCTFE film. Duplex structures are PVC/PCTFE and triplex laminates are PVC/PE/PCTFE. Deeper cavities can be formed by using the triplex structures with PE.

PCTFE films have low water vapor permeation compared to other polymer films used in blister packaging and have thermoforming properties similar to PVC.

COC and COP may be used in multilayered combinations with PP, PE, and/or PETG. Cyclic olefin resins have good thermoforming characteristics and may also be used as a thermoforming enhancer.

Another example of the blister film 102 may include a COC film layer. The COC film layer may be sandwiched between two opposing PP and/or PE layers. The thickness of the outer PP or PE layers may be 10 μm to 50 μm. The thickness of the COC layer may be 150 μm to 400 μm.

In yet another example, the blister film 102 may include cold formed foil layer. A cold formed foil includes an aluminum foil layer sandwiched between polymer layers. In an example, one of the polymer layers is a PVC film and the other polymer layer is a polyamide film. The thickness of the PVC film may be 40 μm to 150 μm. The thickness of the aluminum foil may be 20 μm to 60 μm. The thickness of the polyamide film may be 10 μm to 50 μm.

The blister film 102 may include additives that add functionality, such as radiation barrier and/or moisture absorbing materials.

The lidding foil 108 includes a metal foil such as aluminum foil that is substantially moisture impermeable. The foil may be coated or uncoated with a polymer film such as a polymer film discussed above. In a particular example, an aluminum foil lid closes the cavity 104 and encapsulates the tablet 106 within the blister film 102 and lidding foil 108. The lid may have a thickness of 20 μm to 30 μm or about 25 μm.

The dosage form may be made using conventional tableting excipients and by conventional tableting methods such as blending and compressing the ingredients into the tablet form. In order to impart additional light barrier properties to the tablet, the tablet form itself may include a light barrier outer coating such as an opalescent coating containing mica particles. Such a coating can be applied to the tablet core using conventional tablet coating techniques such as spray coating or the like.

EXAMPLE

This section describes a particular example of a melatonin product packaged in an advantageous blister packaging material that extends the shelf life of the melatonin product.

The melatonin product was REMfresh®, which is commercially available as a tablet dosage form with an opalescent outer coating including mica particles. The outer coating covers a core including melatonin, citric acid, microcrystalline cellulose, hydroxypropyl methylcellulose, and starch.

The blister film includes a PVC film having a thickness of 190.5 μm to 254 μm coated with a polyvinylidene chloride (PVDC) coating having a coating weight of 120+/−6 $g/m^2$. An example of such a blister film material is BlisBa™ DX 120 from Bilcare Research®. This blister film material has a water vapor transmission rate of 0.016 $g/100\ in^2$ per day and an oxygen transmission rate of 0.019 $cm^3/100\ in^2$ per day.

The lidding foil included a 25 μm thick aluminum blister foil with a thin heatseal coating composed of a PVC/PVAC copolymer, including 1% dicarbonic acid mixed with a polymethacrylate. An example of such a lidding foil is AL201CHM™ from Hueck Foils®.

Such a product was observed to have improved storage stability compared to packaging in more conventional packaging materials.

This disclosure has described example embodiments, but not all possible embodiments of the product or materials. Where a particular feature is disclosed in the context of a particular example embodiment, that feature can also be used, to the extent possible, in combination with and/or in the context of other embodiments. The product, materials, and methods may be embodied in many different forms and should not be construed as limited to only the examples described here.

That which is claimed is:

1. A product comprising:
   an oral tablet dosage form including melatonin and citric acid in a polymer matrix;
   a blister film forming a cavity holding the tablet therein, the blister film including a polyvinyl chloride (PVC) film having a thickness of 180 μm to 270 μm coated with a polyvinylidene chloride (PVDC) coating having a coating weight of 110 $g/m^2$ to 130 $g/m^2$; and
   an aluminum foil lid closing the cavity and encapsulating the tablet within the blister film and lid, the lid having a thickness of 20 μm to 30 μm.

2. The product of claim 1, wherein the PVC film has a thickness of 190 μm to 260 μm.

3. The product of claim 1, wherein the PVDC coating has a coating weight of about 120 $g/m^2$.

4. The product of claim 1, wherein the lid has a thickness of about 25 μm.

5. The product of claim 1, wherein the PVC film has a thickness of 190 μm to 260 μm, the PVDC coating has a coating weight of about 120 $g/m^2$, and the lid has a thickness of about 25 μm.

6. The product of claim 1, wherein the tablet includes an opalescent outer coating containing mica particles as a light barrier.

7. The product of claim 1, wherein the tablet dosage form includes at least 5% w/w citric acid.

8. A product comprising:
   an oral tablet dosage form including melatonin and citric acid in a polymer matrix;
   the tablet being enclosed in a packaging material consisting of:
   a blister film forming a cavity holding the tablet therein, the blister film including a polyvinyl chloride (PVC) film having a thickness of 180 μm to 270 μm coated with a polyvinylidene chloride (PVDC) coating having a coating weight of 110 g/m² to 130 g/m²; and an aluminum foil lid closing the cavity and encapsulating the tablet within the blister film and lid, the lid having a thickness of 20 μm to 30 μm and a heatseal coating.

9. The product of claim 8, wherein the PVC film has a thickness of 190 μm to 260 μm.

10. The product of claim 8, wherein the PVDC coating has a coating weight of about 120 g/m².

11. The product of claim 8, wherein the lid has a thickness of about 25 μm.

12. The product of claim 8, wherein the PVC film has a thickness of 190 μm to 260 μm, the PVDC coating has a coating weight of about 120 g/m², and the lid has a thickness of about 25 μm.

13. The product of claim 8, wherein the tablet includes an opalescent outer coating containing mica particles as a light barrier.

14. The product of claim 8, wherein the tablet dosage form includes at least 5% w/w citric acid.

\* \* \* \* \*